(12) United States Patent
Shen et al.

(10) Patent No.: US 8,519,187 B2
(45) Date of Patent: Aug. 27, 2013

(54) PROCESS FOR PRODUCING ORGANIC CARBOXYLIC ACID AMIDES

(75) Inventors: Chia Hui Shen, Kaohsiung County (TW); Chin Yi Lee, Chiayi (TW); Chia Jung Tsai, Kaohsiung (TW)

(73) Assignee: China Petrochemical Development Corp, Taipei (TW)

( * ) Notice: Subject to any disclaimer, the term of this patent is extended or adjusted under 35 U.S.C. 154(b) by 415 days.

(21) Appl. No.: 12/639,284

(22) Filed: Dec. 16, 2009

(65) Prior Publication Data

US 2011/0004020 A1 Jan. 6, 2011

(30) Foreign Application Priority Data

Jul. 3, 2009 (TW) .............................. 98122524 A

(51) Int. Cl.
*C07C 231/06* (2006.01)

(52) U.S. Cl.
USPC .......................................... 564/126; 564/215

(58) Field of Classification Search
USPC .................................................. 564/126, 215
See application file for complete search history.

(56) References Cited

U.S. PATENT DOCUMENTS

| | | | |
|---|---|---|---|
| 3,366,639 | A | 1/1968 | Haefele |
| 4,018,829 | A | 4/1977 | Gruber et al. |
| 4,950,801 | A | 8/1990 | Ebata et al. |
| 4,987,256 | A | 1/1991 | Ebata et al. |
| 5,087,750 | A | 2/1992 | Uda et al. |
| 5,463,123 | A | 10/1995 | Uchiyama |
| 2011/0060159 | A1 | 3/2011 | May et al. |

FOREIGN PATENT DOCUMENTS

| | | |
|---|---|---|
| DE | 2 131 813 | 6/1971 |
| EP | 0 956 898 A2 | 11/1999 |
| FR | 2750987 * | 1/1998 |
| JP | 63-57535 | 6/1986 |
| JP | 63-57534 | 9/1986 |
| JP | 07048330 * | 2/1995 |
| JP | 07070020 * | 3/1995 |
| JP | 07082226 * | 3/1995 |
| TW | 443942 | 5/1999 |
| TW | 200835672 | 11/2006 |

OTHER PUBLICATIONS

Letter of Examination Report from the Taiwanese Intellectual Property Office dated Jan. 31, 2012, No. 01117/10120082220, with translation.
Bennett, M.A. "Homogeneously Catalyzed Hydration of Nitriles to Carboxamides" Journal of the American Chemical Society 95:9, pp. 3030-30310, (1993).
English Language Abstract of JP 63-57534 from Thomson Innovation , 1988.
Kim, Jung Hee "Kinetics and Mechanism of a Co(III) Complex Catalyzed Hydration of Ntiriles" Journal of the American Chemical Society, vol. 115, pp. 3618-6322 (1993).
Komiya, S. "Hydration of 2-Cyanopyridine with Metal Chelates" Chemical Society of Japan, vol. 44, 1440 (1971).
Murahashi, S. "Ruthenium-Catalyzed Hydration of Ntiriles and Transformation of σ-Keto Nitriles to Ene-Lactams" American Chemical Society, vol. 57, pp. 2521-2523 (1992).
Nozaki, F. "Selective Hydration of Acrylonitrile to Acrylamide over a Manganese Dioxide Catalyst" Journal of Catalysis 84, pp. 267-269 (1983).
Sugiyama K "Heterogeneous Hydration of Acrydonitrile over the Metal Oxide Catalysts in Liquid Phase" Bulletin of the Chemical Society of Japan, 59 pp. 2983-2989 (1986).
Villain, G. "Selective Catalysis of the Hydration of Nitriles into Amides. Part II (1) Kinetics Investigation of the Reaction Catalzyed by [PdC(OH)(bipy)(H20)]. Generalization of the Reaction" Journal of the Molecular Catalysis, 12 pp. 103-111(1981).
Wantanabe, K. "Catalytic Hydration of Pyridinecarbonitriles in the Presence of [Cu(en)2CL22H2O and CUCI22H2O" Bulletin of the Chemical Society of Japan vol. 47 No. 8 (1974).

* cited by examiner

*Primary Examiner* — Shailendra Kumar
(74) *Attorney, Agent, or Firm* — Woodard, Emhardt, Moriarty, McNett & Henry LLP

(57) ABSTRACT

The present invention relates to a process for producing organic carboxylic acid amides by nitrile hydrolysis of a nitrile compound at certain temperature and pressure in the presence of a catalyst to produce an organic carboxylic acid amide.

11 Claims, No Drawings

US 8,519,187 B2

PROCESS FOR PRODUCING ORGANIC CARBOXYLIC ACID AMIDES

FIELD OF THE INVENTION

The present invention relates to a process for producing organic carboxylic acid amides by nitrile hydrolysis of a nitrile compound at a certain temperature in the presence of a catalyst to produce an organic carboxylic acid amide. In particular, the present invention relates to a process for producing α-hydroxyl carboxylic acid amides from α-hydroxyl nitrile compounds.

BACKGROUND TO THE INVENTION

Amide compounds have active chemical properties and are involved in various chemical reactions. They are important intermediates in the production of nitriles, amines, etc. and have many industrial uses. For example, acetamide and dimethylformide, which have high dielectric constants, are excellent solvents for many organic and inorganic substances and are widely used in various industries. Acetanilide is an intermediate in the production of sulfonamide medicines, urea is an important raw material for nitrogenous fertilizers and synthetic resins, and caprolactam is the monomer for synthesizing nylon 6.

Most amide compounds are obtained by heating to hydrolyze nitrile compounds in an acidic or basic aqueous solution. However, because amide compounds will continue hydrolyzing to carboxylic acid compounds, the selectivity of this process is not high. Recently, the use of solid acidic materials as a catalyst to solve the drawbacks of the prior art has been extensively discussed and studied, and many catalysts in different forms were successively developed and applied to the selective hydrolysis of nitrile compounds. The catalytic system for use in the hydrolysis of nitrile compounds includes various transition metal catalysts, including copper catalyst [Chem. Soc. Jpn., 44 (1971) 1440] [Bull. Chem. Soc. Jpn., 47 (1974) 1948], palladium catalyst [J. Mol. Catal., 12 (1981) 103], rhodium catalyst [J. Org. Chem., 57 (1992) 2521], platinum catalyst [J. Am. Chem. Soc., 95 (1973) 3030], cobalt catalyst [J. AM. Chem. Soc., 115 (1993) 3618], and nickel catalyst [Bull. Chem. Soc. Jpn., 47 (1974) 1948], which were successively reported to have certain activities when used in the selective hydrolysis of nitrile compounds. However, the aforementioned metal catalysts all cannot be used in industrial processes due to the complex catalytic system and severe reaction conditions.

Currently, manganese dioxide catalyst is the most-reported catalyst for the hydrolysis of nitrile compounds. It has a good catalytic activity for hydrolysis with respect to organic nitrile compounds, of which δ-type manganese dioxide has a higher reaction activity due to its higher surface area [J. Catal., 84 (1983) 267]. The use of manganese dioxide in the hydrolysis of 2-hydroxyisobutyronitrile into α-hydroxyisobutyramide was firstly disclosed in DE 2,131,813. U.S. Pat. No. 4,018,829 discloses the reduction of a heptavalent manganese compound into tetravalent δ-manganese dioxide in a basic environment in a manner of controlling the environmental acidity/basicity, and the use of δ-manganese dioxide as a catalyst for the hydrolysis of 2-hydroxyisobutyronitrile. JP 63-57534 and 63-57535 disclose the use of manganese dioxide in which zinc is incorporated or the use of manganese dioxide obtained by reducing potassium permanganate with a HCl solution, as a catalyst for the hydrolysis of 2-hydroxyisobutyronitrile. It seems that manganese dioxide has been successfully used in the hydrolysis of 2-hydroxyisobutyronitrile and has effectively eliminated the drawbacks of the prior art; however, because the catalytic activity of manganese dioxide is not high, a large amount of catalyst must be used in the process to achieve the desired production of α-hydroxyisobutyramdde. Further, because the reaction activity of manganese dioxide starts to decrease greatly within a very short time, there are also extensive researches and developments on long-life manganese dioxide with high catalytic activity at present. Related researches indicated that the catalytic activity of manganese dioxide is highly related to the preparation method and pretreatment temperature [Bull. Chem. Soc. Jpn., 59 (1986) 2983]. U.S. Pat. No. 4,950,801 discloses that a manganese dioxide catalyst having a large specific surface area, low crystallinity and an amorphous or a nearly amorphous state can be prepared in an acidic environment by introducing at least one kind of Groups IA and IIA metals into manganese dioxide. The modified manganese dioxide catalyst has a higher hydrolysis catalytic activity and a prolonged catalyst life. U.S. Pat. No. 4,987,256 proposes the simultaneous use of manganese (II) and manganese (VII) in a reduction-oxidation reaction to obtain manganese dioxide. The properties of manganese dioxide obtained by this process can be controlled more easily. Also, in the production of manganese dioxide, the sulfates of zirconium, vanadium or zinc are added, whereby the metal zirconium, vanadium or zinc is incorporated into manganese dioxide to improve the activity and life of the catalyst. U.S. Pat. No. 5,087,750 discloses an industrial process for producing α-hydroxyisobutyric acid amide using a fixed bed catalyst in a tubular reactor, which is more suitable for continuous operation, and also proposes that the addition of oxidizing agent in the reactant feed can facilitate prolonging the service lifetime of the manganese dioxide catalyst and increasing the yield of α-hydroxyisobutyric acid amide. U.S. Pat. No. 5,463,123 proposes that the pretreatment of the manganese dioxide catalyst and reducing agent before packing the catalyst in a reactor can suppress the clogging of the by-product oxamide in the catalyst bed during the process, whereby the stability of the catalyst is increased.

Promoting the catalytic activity of manganese dioxide, increasing the stability of the catalyst and prolonging the reaction lifetime of manganese dioxide are key points of the study on modification of the manganese dioxide catalyst. The aforementioned patents all either require using specific preparation processes and/or adding specific promoters to prepare a manganese dioxide catalyst in a specific form, or carrying out a pretreatment of the catalyst before its taking part in the reaction, and adding oxidizing agents during the process, which all result in increasing the complexity of catalyst preparation and reaction operation. In view of the drawbacks of the prior art, the present invention aims to develop a manganese dioxide catalyst that is easily produced, has a high stability and can achieve a commercial level effect within a shorter reaction time.

SUMMARY OF THE INVENTION

The object of the present invention is to provide a process for producing organic carboxylic acid amides from nitrile compounds under a relatively mild reaction condition.

Another object of the present invention is to provide a manganese dioxide catalyst that is easily produced, has a high stability and can achieve a commercial level effect within a shorter reaction time.

According to the present invention, a catalyst comprising a metal oxide and a manganese dioxide active component supported on the metal oxide is used in the hydrolysis of various nitrile compounds to produce organic carboxylic acid amides.

The catalyst for the hydrolysis of nitrile compounds has a structure represented by the formula (I):

$$MnO_2/MO_x \qquad (I)$$

in which M represents a metal of the first to third row transition elements and Groups IIIA and IVA of any valence number, and $MO_x$ represents its metal oxide form such as, for example, iron oxide, nickel oxide, cobalt oxide, niobium oxide, titanium oxide, copper oxide, aluminum oxide, and silicon oxide. $MO_x$ can be a single metal oxide or a mixture of various metal oxides.

According to the present invention, the molar ratio of the manganese dioxide active component to the metal oxide in the catalyst is 0.05-2, preferably 0.1-1.5, and most preferably 0.2-1.2. The catalyst is added in an amount that makes the molar ratio of manganese dioxide to the reacted nitrile compound be between 0.01 and 2, preferably between 0.05 and 1.5, and most preferably between 0.1 and 1.

The nitrile compound used in the present invention has a structure represented by the formula (II):

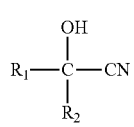

(II)

in which $R_1$ and $R_2$ can be selected from the same or different alkyl group or aryl group. Specifically, $R_1$ can be selected from the group consisting of hydrogen atom, $C_{1-12}$ alkyl group and $C_{6-20}$ aryl group, and $R_2$ can be selected from the group consisting of hydrogen atom, $C_{1-12}$ alkyl group and $C_{6-20}$ aryl group.

According to the present invention, the reaction temperature for the hydrolysis of nitrile compounds is from 30 to 160° C., preferably from 30 to 140° C., and most preferably from 30 to 120° C.; the reaction pressure is from 0 to 2 kg/cm²; and the reaction time is from 0.2 to 8 hours. The reaction is an equilibrium reaction, and the yield of the reaction depends on the kind and amount of the nitrile compound as used.

Compared with the aforementioned prior art, the use of the catalyst of a manganese dioxide active component supported on a metal oxide according to the present invention can effectively increase the dispersivity of the manganese dioxide active component and really promote its catalytic activity; also, as the manganese dioxide active component is protected by the metal oxide, its stability is enhanced and the selectivity of the reaction can thus be maintained so that a commercial level effect can be achieved within a shorter reaction time.

The features and effects of the present invention will be further explained with reference to the preferred embodiments below, which are, however, not intended to restrict the scope of the present invention.

DESCRIPTION OF PREFERRED EMBODIMENTS

The convertibility and selectivity used in the specification are calculated according to the following equations:

Convertibility (%)={[Concentration of Added Nitrile Compound−Concentration of Unreacted Nitrile Compound] (mol)/Concentration of Added Nitrile Compound (mol)}×100%

Selectivity (%)=[Concentration of Organic Carboxylic Acid Amide in the Product (mol)/Concentration of Consumed Nitrile Compound (mol)]×100%

The catalyst of the present invention is suitable to selective hydrolysis of various nitrile compounds. The following embodiments are provided to facilitate understanding of the contents of the present invention only but do not restrict the practical scope of the present invention.

COMPARATIVE EXAMPLE 1

(1) Preparation of Catalyst

In a 500-ml three-necked bottle, 21.11 g of potassium permanganate, 33.76 g of manganese sulfate, 14 g of a concentrated sulfuric acid solution and 270 g of deionized water were mixed evenly. After a reaction thereof for 3 hours at a temperature of 70° C., a suction filtration was performed. The product was rinsed with deionized water and then dried in a vacuum oven. Thus a desired $MnO_2$ catalyst was obtained.

(2) Hydrolysis Test

A reaction of 15 g (0.176 mol) of 2-hydroxyisobutyronitrile, 10 g (0.172 mol) of acetone, 35 g (1.944 mol) of deionized water and 6 g (0.069 mol) of the $MnO_2$ catalyst, placed in a 250-ml three-necked bottle, was carried out with a reflux method in a batch operation at a temperature of 60° C. and a rotation rate of 400 rpm. Samplings were conducted at 3 hours and 5 hours after the reaction was initiated. The product was analyzed with high pressure liquid chromatography. The result is shown in Table 1.

EXAMPLE 1

(1) Preparation of Catalyst

In a 500-ml three-necked bottle, 21.11 g of potassium permanganate, 8.647 g of cobalt oxide, 33.76 g of manganese sulfate, 14 g of a concentrated sulfuric acid solution and 270 g of deionized water were mixed evenly. After a reaction thereof for 3 hours at a temperature of 70° C., a suction filtration was performed. The product was rinsed with deionized water and then dried in a vacuum oven. Thus a desired $MnO_2/CO_3O_4$ catalyst (Mn/Co molar ratio=1) was obtained.

(2) Hydrolysis Test

A reaction of 15 g (0.176 mol) of 2-hydroxyisobutyronitrile, 10 g (0.172 mol) of acetone, 35 g (1.944 mol) of deionized water and 11.537 g of the $MnO_2/CO_3O_4$ catalyst (0.069 mol of Mn), placed in a 250-ml three-necked bottle, was carried out with a reflux method in a batch operation at a temperature of 60° C. and a rotation rate of 400 rpm. Samplings were conducted at 3 hours and 5 hours after the reaction was initiated. The product was analyzed with high pressure liquid chromatography. The result is shown in Table 1.

TABLE 1

| No. | Catalyst | Mn/ M Molar Ratio | 3 Hr Conv. (%) | Sel. (%) | 5 Hr Conv. (%) | Sel. (%) |
|---|---|---|---|---|---|---|
| CEx. 1 | $MnO_2$ | — | 86.88 | 95.88 | 91.21 | 94.65 |
| Ex. 1 | $MnO_2/Co_3O_4$ | 1 | 88.81 | 99.41 | 96.28 | 94.31 |

CEx. = Comparative Example
Ex. = Example

The experimental results in Table 1 show that manganese dioxide supported on a metal oxide can effectively promote the reaction activity of manganese dioxide, shorten the reaction time, maintain the selectivity of α-hydroxyisobutyramide, and achieve a commercial level effect within a reaction time of 3 hours.

EXAMPLES 2-7

(1) Preparation of Catalyst

The catalysts were prepared in the same manner as in Example 1, except that cobalt oxide in Example 1 was replaced with other metal oxides listed in Table 2, with the molar ratio of manganese to individual metal being 1.

(2) Hydrolysis Test

The hydrolysis tests were conducted in the same manner as in Example 1 with the $MnO_2/MO_x$ catalysts having 0.069 mol of Mn (i.e. Mn/M molar ratio=1) used. The results are shown in Table 2.

TABLE 2

| No. | Catalyst | Mn/M Molar Ratio | 3 Hr Conv. (%) | 3 Hr Sel. (%) | 5 Hr Conv. (%) | 5 Hr Sel. (%) |
|---|---|---|---|---|---|---|
| Ex. 2 | $MnO_2/Nb_2O_5$ | 1 | 86.76 | 95.32 | 91.98 | 95.60 |
| Ex. 3 | $MnO_2/NiO$ | 1 | 74.10 | 90.41 | 92.48 | 90.39 |
| Ex. 4 | $MnO_2/TiO_2$ | 1 | 82.29 | 93.39 | 88.44 | 93.72 |
| Ex. 5 | $MnO_2/Fe_2O_3$ | 1 | 80.18 | 92.69 | 89.17 | 93.93 |
| Ex. 6 | $MnO_2/Al_2O_3$ | 1 | 59.34 | 83.24 | 82.48 | 85.57 |
| Ex. 7 | $MnO_2/SiO_2$ | 1 | 88.40 | 94.68 | 92.32 | 94.24 |

Ex. = Example

The experimental results in Table 2 show that different kinds of metal oxides can be used as a carrier supporting the manganese dioxide active component and maintain certain reaction activity levels.

EXAMPLES 8-9

(1) Preparation of Catalyst

The catalysts were prepared in the same manner as in Example 1, except that the added amount of cobalt oxide in Example 1 was altered to make the molar ratio of manganese to cobalt be 0.5 and 0.2, respectively.

(2) Hydrolysis Test

The hydrolysis tests were conducted in the same manner as in Example 1 with the $MnO_2/CO_2O_4$ catalysts having 0.069 mol of Mn used. The results are shown in Table 3.

TABLE 3

| No. | Catalyst | Mn/Co Molar Ratio | 3 Hr Conv. (%) | 3 Hr Sel. (%) | 5 Hr Conv. (%) | 5 Hr Sel. (%) |
|---|---|---|---|---|---|---|
| Ex. 1 | $MnO_2/Co_3O_4$ | 1 | 88.81 | 99.41 | 96.28 | 94.31 |
| Ex. 8 | $MnO_2/Co_3O_4$ | 0.5 | 82.74 | 92.19 | 94.21 | 94.65 |
| Ex. 9 | $MnO_2/Co_3O_4$ | 0.2 | 70.80 | 92.06 | 85.14 | 92.35 |

Ex. = Example

The experimental results in Table 3 show that the added amount of the metal oxide will affect the reaction activity of the whole $MnO_2/MO_x$ catalyst.

EXAMPLE 10

(1) Preparation of Catalyst

The catalyst was prepared in the same manner as in Example 1, except that cobalt oxide in Example 1 was replaced with a mixture of cobalt oxide and aluminum oxide in which the Co/Al molar ratio was equal to 1 while the molar ratio of manganese to the metal in the metal oxide was 1. Thus a desired $MnO_2/CO_3O_4$—$Al_2O_3$ catalyst (Mn/(Co+Al) molar ratio=1, Co/Al molar ratio=1) was obtained.

(2) Hydrolysis Test

The hydrolysis test was conducted in the same manner as in Example 1 with the $MnO_2/CO_3O_4$—$Al_2O_3$ catalyst having 0.069 mol of Mn used. The result is shown in Table 4.

EXAMPLES 11-12

(1) Preparation of Catalyst

The catalysts were prepared in the same manner as in Example 1, except that the Co/Al molar ratio in the mixture of cobalt oxide and aluminum oxide in Example 10 was altered to 0.33 and 0.20, respectively, while the molar ratio of manganese to the metal in the metal oxide remained 1. Thus a desired $MnO_2/CO_3O_4$—$Al_2O_3$ catalyst (Mn/(Co+Al) molar ratio=1, Co/Al molar ratio=0.33) and $MnO_2/CO_3O_4$—$Al_2O_3$ catalyst (Mn/(Co+Al) molar ratio=1, Co/Al molar ratio=0.20) were obtained.

(2) Hydrolysis Test

The hydrolysis tests were conducted in the same manner as in Example 1 with the $MnO_2/CO_3O_4$—$Al_2O_3$ catalysts having 0.069 mol of Mn used. The results are shown in Table 4.

TABLE 4

| No. | Catalyst | Mn/(Co + Al) Molar Ratio | Co/Al Molar Ratio | 3 Hr Conv. (%) | 3 Hr Sel. (%) | 5 Hr Conv. (%) | 5 Hr Sel. (%) |
|---|---|---|---|---|---|---|---|
| Ex. 1 | $MnO_2/Co_3O_4$ | 1 | — | 88.81 | 99.41 | 96.28 | 94.31 |
| Ex. 10 | $MnO_2/Co_3O_4$—$Al_2O_3$ | 1 | 1 | 85.10 | 92.24 | 89.71 | 92.51 |
| Ex. 11 | $MnO_2/Co_3O_4$—$Al_2O_3$ | 1 | 0.33 | 84.34 | 91.33 | 91.21 | 90.86 |
| Ex. 12 | $MnO_2/Co_3O_4$—$Al_2O_3$ | 1 | 0.20 | 79.41 | 92.61 | 85.93 | 92.64 |

Ex. = Example

The experimental results in Table 4 show that the metal oxide for supporting manganese dioxide can be a single metal oxide or a mixture of various metal oxides.

COMPARATIVE EXAMPLE 2

(1) Preparation of Catalyst

The $MnO_2$ catalyst was prepared in the same manner as in Comparative Example 1.

(2) Hydrolysis Test

The hydrolysis test was conducted in the same manner as in Comparative Example 1 with the $MnO_2$ catalyst having 0.046 mol of Mn used. The result is shown in Table 5.

EXAMPLES 13-15

(1) Preparation of Catalyst

The $MnO_2/CO_3O_4$ catalysts (Mn/Co molar ratio=1) were prepared in the same manner as in Example 1.

(2) Hydrolysis Test

The hydrolysis tests were conducted in the same manner as in Example 1 with the $MnO_2/MO_x$ catalysts having 0.130 mol, 0.046 mol and 0.023 mol of Mn (Mn/M molar ratio=1) used. The results are shown in Table 5.

TABLE 5

| No. | Catalyst | Mn/Co Molar Ratio | MnO$_2$/ACH Molar Ratio | 3 Hr Conv. (%) | 3 Hr Sel. (%) | 5 Hr Conv. (%) | 5 Hr Sel. (%) |
|---|---|---|---|---|---|---|---|
| CEx. 1 | MnO$_2$ | — | 0.368 | 86.88 | 95.88 | 91.21 | 94.65 |
| CEx. 2 | MnO$_2$ | — | 0.245 | 72.19 | 93.49 | 76.23 | 93.28 |
| Ex. 13 | MnO$_2$/Co$_3$O$_4$ | 1 | 0.736 | 92.29 | 95.33 | 92.48 | 94.30 |
| Ex. 1 | MnO$_2$/Co$_3$O$_4$ | 1 | 0.368 | 88.81 | 99.41 | 96.28 | 94.31 |
| Ex. 14 | MnO$_2$/Co$_3$O$_4$ | 1 | 0.245 | 79.18 | 94.79 | 89.39 | 93.91 |
| Ex. 15 | MnO$_2$/Co$_3$O$_4$ | 1 | 0.184 | 54.80 | 94.75 | 66.74 | 94.89 |

CEx. = Comparative Example
Ex. = Example

The experimental results in Table 5 show that manganese dioxide supported on a metal oxide can really facilitate promoting the catalytic activity, maintain the selectivity, and effectively shorten the reaction time or reduce the amount of used catalyst.

EXAMPLES 16-18

(1) Preparation of Catalyst
The MnO$_2$/CO$_3$O$_4$ catalysts (Mn/Co molar ratio=1) were prepared in the same manner as in Example 1.
(2) Hydrolysis Test
The hydrolysis tests were conducted at temperatures of 50° C., 80° C. and 100° C. in the same manner as in Example 1. The results are shown in Table 6.

TABLE 6

| No. | Catalyst | Mn/Co Molar Ratio | Temp. (° C.) | 3 Hr Conv. (%) | 3 Hr Sel. (%) | 5 Hr Conv. (%) | 5 Hr Sel. (%) |
|---|---|---|---|---|---|---|---|
| Ex. 16 | MnO$_2$/Co$_3$O$_4$ | 1 | 50 | 68.31 | 94.06 | 80.20 | 95.17 |
| Ex. 1 | MnO$_2$/Co$_3$O$_4$ | 1 | 60 | 88.81 | 99.41 | 96.28 | 94.31 |
| Ex. 17 | MnO$_2$/Co$_3$O$_4$ | 1 | 80 | 92.72 | 88.03 | 95.86 | 89.88 |
| Ex. 18 | MnO$_2$/Co$_3$O$_4$ | 1 | 100 | 94.01 | 86.23 | 95.69 | 85.47 |

Ex. = Example

The experimental results in Table 6 show that the increase in reaction temperature can facilitate promoting the reaction rate but may result in the decrease of selectivity.

EXAMPLE 19

(1) Preparation of Catalyst
The MnO$_2$/CO$_3$O$_4$ catalyst (Mn/Co molar ratio=1) was prepared in the same manner as in Example 1.
(2) Hydrolysis Test
A reaction of 12.53 g (0.176 mol) of 2-hydroxypropanenitrile, 10 g (0.172 mol) of acetone, 35 g (1.944 mol) of deionized water and 11.537 g of the MnO$_2$/CO$_3$O$_4$ catalyst (0.069 mol of Mn), placed in a 250-ml three-necked bottle, was carried out with a reflux method in a batch operation at a temperature of 60° C. and a rotation rate of 400 rpm. Samplings were conducted at 3 hours and 5 hours after the reaction was initiated. The product was analyzed with high pressure liquid chromatography. The result is shown in Table 7.

EXAMPLE 20

(1) Preparation of Catalyst
The MnO$_2$/CO$_3$O$_4$ catalyst (Mn/Co molar ratio=1) was prepared in the same manner as in Example 1.
(2) Hydrolysis Test
A reaction of 24.43 g (0.176 mol) of mandelonitrile, 10 g (0.172 mol) of acetone, 35 g (1.944 mol) of deionized water and 11.537 g of the MnO$_2$/CO$_3$O$_4$ catalyst (0.069 mol of Mn), placed in a 250-ml three-necked bottle, was carried out with a reflux method in a batch operation at a temperature of 60° C. and a rotation rate of 400 rpm. Samplings were conducted at 3 hours and 5 hours after the reaction was initiated. The product was analyzed with high pressure liquid chromatography. The result is shown in Table 7.

TABLE 7

| No. | Nitrile Compound | Catalyst | 3 Hr Conv. (%) | 3 Hr Sel. (%) | 5 Hr Conv. (%) | 5 Hr Sel. (%) |
|---|---|---|---|---|---|---|
| Ex. 1 | 2-hydroxyisobutyronitrile | MnO$_2$/Co$_3$O$_4$ | 88.81 | 99.41 | 96.28 | 94.31 |
| Ex. 19 | 2-hydroxypropanenitrile | MnO$_2$/Co$_3$O$_4$ | 96.65 | 98.31 | 98.70 | 98.07 |
| Ex. 20 | mandelonitrile | MnO$_2$/Co$_3$O$_4$ | 57.63 | 70.58 | 64.71 | 66.53 |

Ex. = Example

The experimental results in Table 7 show that the catalytic system of the present invention is suitable to the hydrolysis of various nitrile compounds to produce organic carboxylic acid amides.

What is claimed is:

1. A process for producing organic carboxylic acid amides by nitrile hydrolysis of a nitrile compound in the presence of a catalyst to produce an organic carboxylic acid amide, wherein the catalyst comprises a manganese dioxide active component supported on $Co_3O_4$, and wherein the molar ratio of the manganese dioxide active component to the $Co_3O_4$ is 0.05:1 to 2:1.

2. The process according to claim 1, wherein the molar ratio of the manganese dioxide active component to the metal oxide is 0.1-1.5.

3. The process according to claim 2, wherein the molar ratio of the manganese dioxide active component to the metal oxide is 0.2-1.2.

4. The process according to claim 1, wherein the nitrile compound has a structure represented by the formula (II):

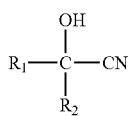

(II)

in which $R_1$ and $R_2$ are the same or different and are independently selected from the group consisting of hydrogen atom, $C_{1-12}$ alkyl group and $C_{6-20}$ aryl group.

5. The process according to claim 1, wherein the nitrile hydrolysis reaction is carried out at a temperature of from 30 to 160° C.

6. The process according to claim 5, wherein the nitrile hydrolysis reaction is carried out at a temperature of from 30 to 140° C.

7. The process according to claim 6, wherein the nitrile hydrolysis reaction is carried out at a temperature of from 30 to 120° C.

8. The process according to claim 1, wherein the nitrile hydrolysis reaction is carried out at a pressure of from 0 to 2 kg/cm2.

9. The process according to claim 1, wherein the catalyst is added in an amount that makes the molar ratio of manganese dioxide to the reacted nitrile compound be between 0.01 and 2.

10. The process according to claim 9, wherein the catalyst is added in an amount that makes the molar ratio of manganese dioxide to the reacted nitrile compound be between 0.05 and 1.5.

11. The process according to claim 10, wherein the catalyst is added in an amount that makes the molar ratio of manganese dioxide to the reacted nitrile compound be between 0.1 and 1.

* * * * *